(12) United States Patent
Morita et al.

(10) Patent No.: US 7,347,926 B2
(45) Date of Patent: Mar. 25, 2008

(54) METHOD AND APPARATUS FOR MEASURING SPECIFIC COMPONENT

(75) Inventors: Yoshimitsu Morita, Kyoto (JP); Yoshimi Oura, Kyoto (JP)

(73) Assignee: Arkray, Inc., Kyoto (JP)

( * ) Notice: Subject to any disclaimer, the term of this patent is extended or adjusted under 35 U.S.C. 154(b) by 758 days.

(21) Appl. No.: 10/493,752

(22) PCT Filed: Oct. 22, 2002

(86) PCT No.: PCT/JP02/10967

§ 371 (c)(1),
(2), (4) Date: Apr. 26, 2004

(87) PCT Pub. No.: WO03/036285

PCT Pub. Date: Jan. 5, 2003

(65) Prior Publication Data

US 2004/0259264 A1   Dec. 23, 2004

(30) Foreign Application Priority Data

Oct. 26, 2001   (JP) ............................. 2001-328790

(51) Int. Cl.
*G01N 27/327*   (2006.01)
*G01N 27/403*   (2006.01)

(52) U.S. Cl. ................... 205/792; 205/777.5; 205/775; 204/403.01; 204/400; 204/403.14; 204/403.02

(58) Field of Classification Search ...............
204/403.01–403.15, 416–419; 205/775, 205/777.5, 792
See application file for complete search history.

(56) References Cited

U.S. PATENT DOCUMENTS

| 4,396,464 | A |   | 8/1983  | Giner et al. ................. 205/786   |
| 5,352,351 | A | * | 10/1994 | White et al. ........... 204/403.04     |
| 5,620,579 | A |   | 4/1997  | Genshaw et al. ...... 204/403.11        |

FOREIGN PATENT DOCUMENTS

| EP | 0 741 186 A2 | 4/1996 |
| EP | 1 081 490 A1 | 5/1999 |
| JP | 57-88365     | 6/1982 |
| JP | 62-168045    | 7/1987 |
| JP | 63-259457    | 10/1988 |
| JP | 4-357452     | 12/1992 |
| JP | 8-10208      | 1/1996 |
| JP | 9-201337     | 8/1997 |
| JP | 2001-91512   | 4/2001 |

* cited by examiner

*Primary Examiner*—Alex Noguerola
(74) *Attorney, Agent, or Firm*—Hamre, Schumann, Mueller & Larson, P.C.

(57) ABSTRACT

A method for measuring a concentration of a specific component includes the steps of: supplying a sample fluid to a reaction field holding a reagent; obtaining a single or a plurality of leak currents for correction, through a measurement of electric current made once or a plurality of times without applying a voltage to the reaction field; obtaining a single or a plurality of electric currents for calculation, through a measurement of electric current made once or a plurality of times while applying a voltage to the reaction field; and calculating a concentration of a specific component in the sample fluid, based on the single or the plurality of values for correction and the single or the plurality of values for calculation.

11 Claims, 6 Drawing Sheets

FIG.7

| Hct | 20% | | 35% | | 45% | | 55% | | 70% | |
|---|---|---|---|---|---|---|---|---|---|---|
| Glucose Level (mg/dL) | Uncorrected | Corrected | Uncorrected | Corrected | Uncorrected | Corrected | Uncorrected | Corrected | Uncorrected | Corrected |
| Average Response Current | 600 | 416.5 mV | 416.1 mV | 370.8 mV | 369.9 mV | 344.4 mV | 342.8 mV | 308.7 mV | 308.5 mV | 241.6 mV | 242.1 mV |
| | 300 | 210.7 mV | 212.5 mV | 194.3 mV | 195.1 mV | 183.1 mV | 183.7 mV | 171.2 mV | 171.6 mV | 132.3 mV | 133.3 mV |
| | 100 | 65.4 mV | 66.0 mV | 63.4 mV | 63.5 mV | 62.8 mV | 62.9 mV | 61.9 mV | 61.9 mV | 58.3 mV | 58.1 mV |
| | 20 | 26.9 mV | 27.5 mV | 26.6 mV | 26.7 mV | 26.8 mV | 26.6 mV | 27.3 mV | 27.0 mV | 28.0 mV | 27.5 mV |
| Standard Deviation | 600 | 18.31 | 17.64 | 12.64 | 12.52 | 12.36 | 12.03 | 11.94 | 11.36 | 9.07 | 8.71 |
| | 300 | 11.85 | 11.32 | 4.74 | 4.44 | 4.44 | 4.31 | 4.61 | 4.50 | 5.31 | 4.43 |
| | 100 | 2.60 | 2.46 | 3.08 | 2.70 | 3.16 | 2.59 | 3.10 | 2.53 | 4.18 | 3.41 |
| | 20 | 1.88 | 1.63 | 1.87 | 1.50 | 2.03 | 1.65 | 2.30 | 1.89 | 2.57 | 2.15 |
| Reproducibility | 600 | 4.40% | 4.24% | 3.41% | 3.38% | 3.59% | 3.51% | 3.87% | 3.68% | 3.76% | 3.60% |
| | 300 | 5.62% | 5.33% | 2.44% | 2.28% | 2.43% | 2.35% | 2.69% | 2.62% | 4.02% | 3.32% |
| | 100 | 3.98% | 3.73% | 4.86% | 4.25% | 5.03% | 4.12% | 5.00% | 4.09% | 7.17% | 5.82% |
| | 20 | 6.97% | 5.93% | 7.04% | 5.60% | 7.57% | 6.22% | 8.43% | 7.01% | 9.18% | 7.80% |

METHOD AND APPARATUS FOR MEASURING SPECIFIC COMPONENT

This application is a 371 of PCT/JP02/10967, filed Oct. 22, 1002, which claims priority from Japanese application no. 2001-328790, filed Oct. 26, 2001.

TECHNICAL FIELD

The present invention relates to a method and an apparatus for measuring a specific component in a sample fluid, such as a glucose level in blood.

BACKGROUND ART

As a common method of measuring a concentration of a specific component in a body fluid (such as glucose in blood), an oxidation-reduction reaction is used. On the other hand, for handy measurement of the blood glucose levels at home and elsewhere, palm-size, portable blood glucose level testers are used widely. These handy-type blood glucose level testers make use of a disposable biosensor which is attached to the tester and serves as an enzyme reaction field. The blood glucose level measurement is made by supplying the blood to the biosensor (See JP-B 8-10208 for example.)

The biosensor includes, for example, a substrate provided with a pair of electrodes and a reagent pad bridging the electrodes. The reagent pad includes, for example, an oxidation-reduction enzyme and an electron transfer material in an oxidized form. When the reagent pad is supplied with a sample fluid, the reagent pad and the sample fluid constitute a liquid phase reaction system. In this liquid phase reaction system, the oxidation-reduction enzyme promotes oxidation of blood glucose and release of electrons while the electron transfer material is supplied with the electrons and thereby reduced.

The blood glucose level tester, on the other hand, includes a voltage source and an electric current measurer for example. When the biosensor is attached to the blood glucose level tester, an electric circuit is formed by the reagent pad (liquid phase reaction system), the voltage source and the electric current measurer. The voltage source applies a voltage between the pair of electrodes of the biosensor. When the voltage is applied between the electrodes, a chemical reaction reduces the electron transfer material, which releases electrons to one of the electrodes, causing oxidation. The amount of electrons released and the current passed through the circuit at this time are measured by the electric current measurer.

In the measurement of the blood glucose level, the voltage applied to the reagent pad (liquid phase reaction system) and the current measured are generally in a relationship shown in FIG. 4.

Specifically, from the time when blood is supplied to the reagent pad of the biosensor which is attached to the blood glucose level tester to the time when the supply of the blood to the reagent pad is detected (FIG. 4, $t_1 \rightarrow t_2$), a constant voltage V is applied to the electrodes of the biosensor. During this time, the supply of the blood to the reagent pad increases the measured current, and at a point (FIG. 4, $t_2$) when the measured current has reached a predetermined value (FIG. 4, $I_1$), the blood glucose level tester determines that the sample fluid has been supplied. On the other hand, upon the detection of the blood supply, the application of the voltage is stopped for a predetermined duration of time (FIG. 4, $t_2 \rightarrow t_3$). Upon passage of the predetermined duration of time (FIG. 4, $t_3$) since the detection of blood supply, application of the constant voltage V is resumed between the electrodes of the biosensor. During this time, the electron transfer material which has been reduced releases electrons to one of the electrodes of the biosensor. The amount of the released electrons is measured as a response current $I_2$ at a time point (FIG. 4, $t_4$) when a predetermined amount of time has been passed since the reapplication of the voltage, and calculations are made for the concentration of the specific component based on the response current $I_2$.

When the biosensor is attached to the blood glucose level tester, a circuit is formed as described earlier, by the biosensor electrodes, the source of voltage and the electric current measurer. In order to turn off the voltage to the reagent pad (the liquid phase reaction system), the electric circuit may simply be opened, and opening the circuit is easily be made by providing a mechanical switch and turning it off in the circuit. Disadvantages of this method however, include a high cost incurred by the mechanical switch, and low reliability due to potential failure of the mechanical switch. For these reasons, when cost and reliability are factors of concern, a method is used in which the voltage supplied from the voltage source is turned to zero, without using a mechanical switch. In this method however, the circuit is not opened as completely as by a mechanical switch. Therefore, if there is a difference in electric potential in the circuit, electromotive force in the reagent pad (liquid phase reaction system) can cause a small amount of electric current to pass through the circuit.

Once such an electric potential difference occurs in the reagent pad (liquid phase reaction system), an amount of the electron transfer material in the reduced form for example is oxidized to release electrons, and these electrons will move to one of the biosensor electrodes. In another occasion, the electron transfer material in the oxidized form is supplied with electrons from one of the biosensor electrodes to become the reduced form. Under such an occasion, as shown in FIG. 5, the measurement of the response current may give a lower value ($I_2'$) or a higher value ($I_2''$) than the real value ($I_2$). As a result, the blood glucose level which is the final target value will be different from the real blood glucose level, and each measurement will give an inconsistent value.

DISCLOSURE OF THE INVENTION

It is therefore an object of the present invention to provide an electrochemical method capable of measuring a concentration of a specific component in a sample fluid.

A first aspect of the present invention provides a method for measuring a concentration of a specific component. The method includes: a first step of supplying a sample fluid to a reaction field holding a reagent; a second step of obtaining a single or a plurality of electric currents for correction, through a measurement of electric current made once or a plurality of times without applying a voltage to the reaction field; a third step of obtaining a single or a plurality of electric currents for calculation, through a measurement of electric current made once or a plurality of times while applying a voltage to the reaction field; and a fourth step of calculating a concentration of a specific component in the sample fluid, based on the single or the plurality of values for correction and the single or the plurality of values for calculation.

Preferably, the fourth step reflects an average or cumulative value of the electric currents for correction on a calculated result of the concentration of the specific component.

In order to reflect the average or cumulative value on the calculated result of the concentration of the specific component, the following three options can be exemplified:

A first option is to include in the fourth step: calculation of a correction constant based on the electric currents for correction; conversion of the single electric current for calculation into a voltage for calculation, calculation of a corrected voltage by adding the correction constant to the voltage for calculation; and calculation of a final concentration of the specific component from the corrected voltage.

According to this option, the calculation of the correction constant is made, for example, by adding a constant to one of the values selected from: a first voltage conversion value for correction given as an average of voltage conversion values converted from the measurements for correction; a second voltage conversion value for correction given as a cumulative value of the voltage conversion values converted from the measurements for correction; and a third voltage conversion value for correction given as a voltage conversion value converted from an average or cumulative value of the electric currents for correction.

A second option is to include in the fourth step: calculation of a correction constant based on an average or cumulative value of the electric currents for correction; calculation of a corrected current by adding the correction constant to the electric current for calculation; and calculation of a final concentration of the specific component based on the corrected current.

A third option is to include in the fourth step: calculation of a preliminary concentration of the specific component from the single or the plurality of currents for calculation; calculation of a correction constant based on an average or cumulative value of the electric currents for correction; and calculation of a final concentration of the specific component by adding the correction constant to the preliminary concentration.

A second aspect of the present invention provides a concentration measuring apparatus for measurement of a concentration of a specific component in a sample fluid by using a measuring tool for holding the sample fluid and providing a reaction field. The measuring tool includes a first and a second electrodes for application of a voltage to the reaction field, and the apparatus comprises: a voltage applier for application of a voltage to the reaction field; a controller for selection from an energized state in which the voltage is applied to the reaction field and a de-energized state in which a voltage is not applied to the reaction field; an electric current measurer for measurement of an electric current for calculation, by using the first and the second electrodes; and an arithmetic processor for calculation of a concentration of the specific component based on the electric current for calculation. The controller selects the de-energized state for a specific duration of time after a supply of the sample fluid to the reaction field, and selects the energizing state for at least a predetermined period of time after passage of the specific duration of time. The electric current measurer obtains a single or a plurality of electric currents for correction through a measurement of electric current made once or a plurality of times during the specific duration of time, and the arithmetic processor calculates the concentration of the specific component while taking into account the single or the plurality of electric currents for correction.

According to a preferred embodiment, the arithmetic processor reflects an average or cumulative value of the measurements on a calculated result of the concentration of the specific component.

According to the present invention, the reagent held by the measuring tool contains, for example, an oxidation-reduction enzyme and an electron transfer material.

According to the present invention, the sample fluid is typically a body fluid such as blood and urine, whereas the specific component is typically glucose, cholesterol and lactic acid.

BRIEF DESCRIPTION OF THE DRAWINGS

FIG. 7 is a table showing uncorrected and corrected values in each sample group in the graph in FIG. 6.

BEST MODE FOR CARRYING OUT THE INVENTION

Hereinafter, the best mode for carrying out the present invention will be described with reference to the drawings.

Figure 1:
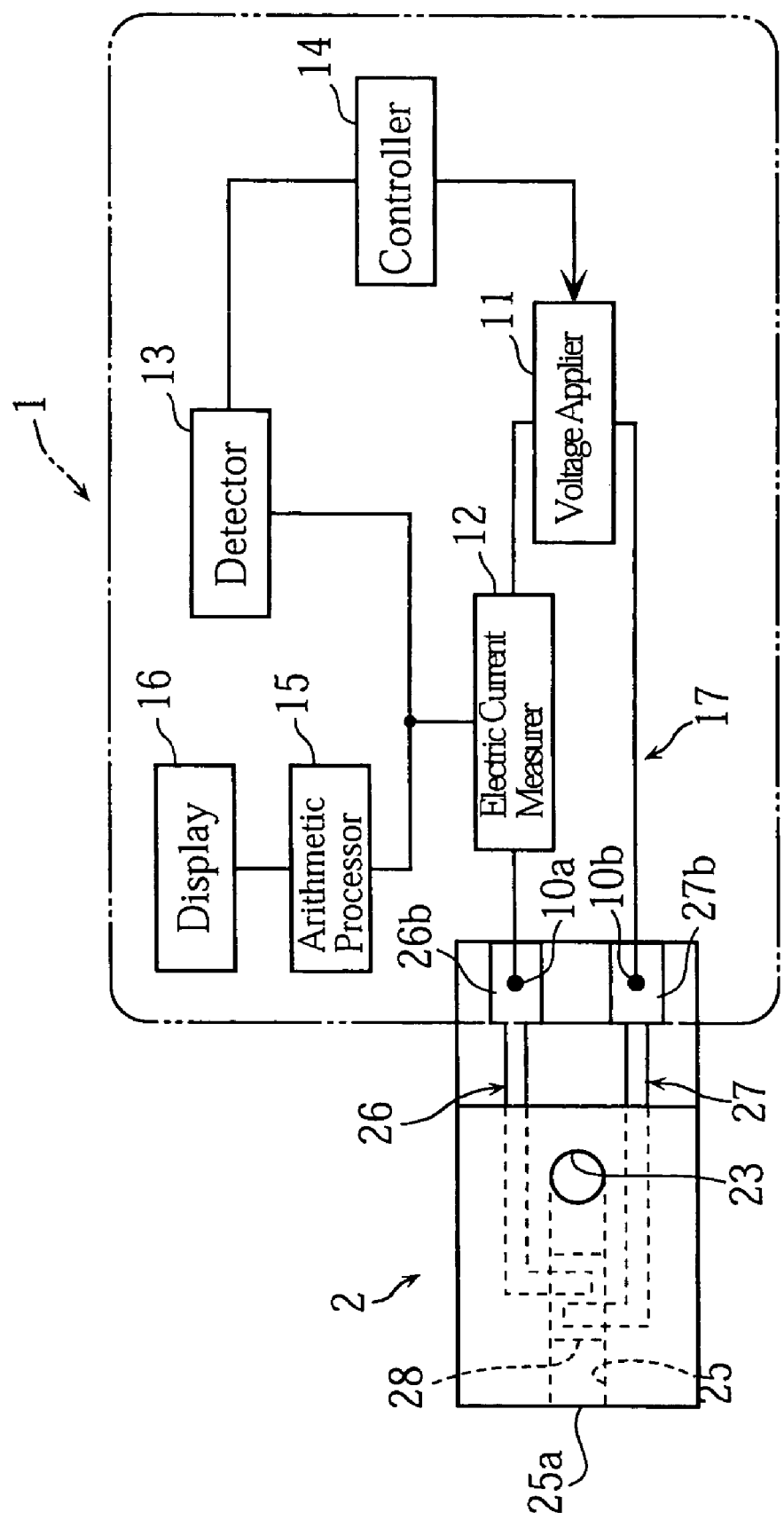
FIG. 1 shows a case in which a biosensor is attached to a concentration measuring apparatus according to the present invention: the concentration measuring apparatus is shown in a block diagram whereas the biosensor is shown in a plan view.

FIG. 1 shows a concentration measuring apparatus 1, which is an apparatus for measuring the concentration of a specific component in a sample fluid by using a biosensor 2, and includes a first and a second terminals 10a, 10b, a voltage applier 11, an electric current measurer 12, a detector 13, a controller 14, an arithmetic processor 15 and a display 16.

Figure 2:
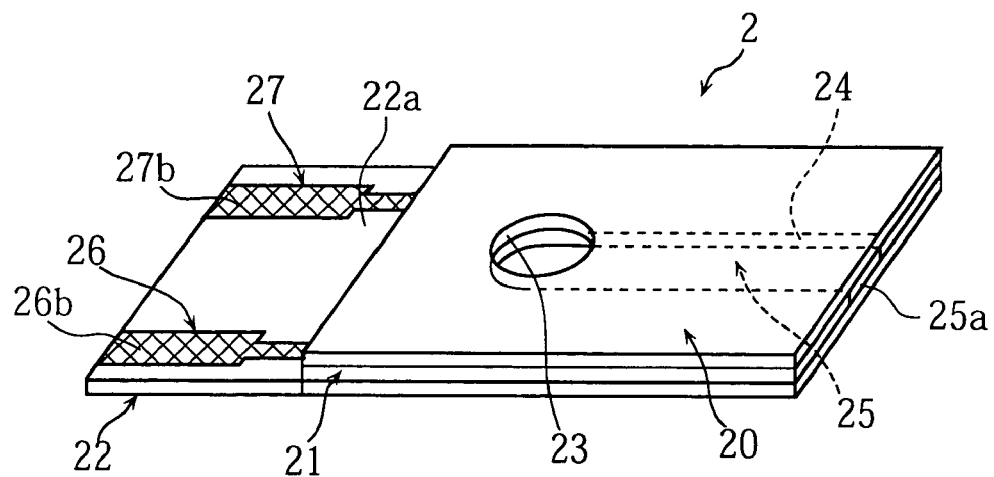
FIG. 2 is an overall perspective view of the biosensor in FIG. 1.
Figure 3:
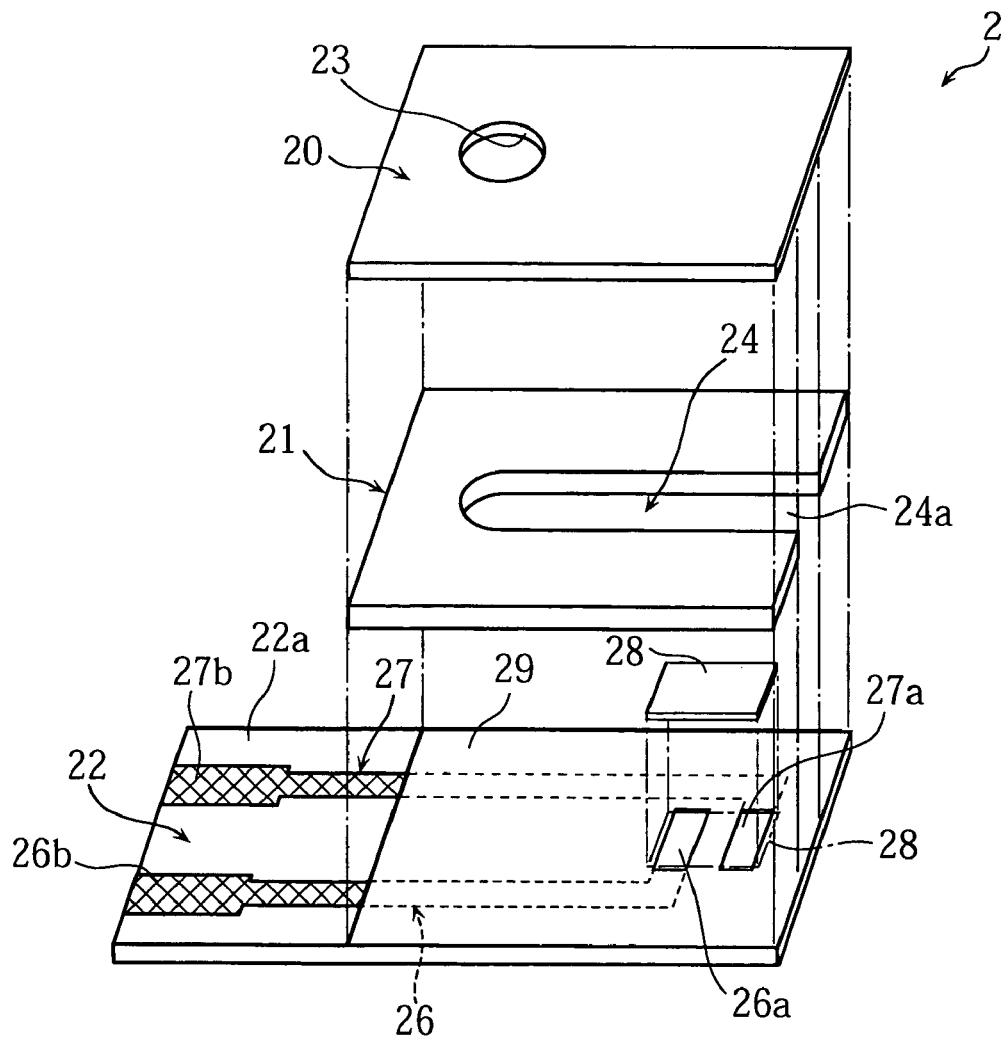
FIG. 3 is an exploded perspective view of the biosensor in FIG. 2.

The biosensor 2 includes, as clearly shown in FIG. 2 and FIG. 3, a cover 20, a spacer 21 and a substrate 22 which collectively provide a passage 25.

The passage 25 communicates with outside via a hole 23 provided in the cover 20 and a tip opening 24a of a slit 24 provided in the spacer 21. The tip opening 24a serves as a sample fluid entrance 25a. The sample fluid introduced in the sample liquid entrance 25a moves through the passage 25 toward the hole 23 by capillary action.

The substrate 22 is made of a resin such as PET, into a generally rectangular shape. The substrate 22 has an upper surface 22a provided with a working electrode 26, an counter electrode 27 and a reagent pad 28.

The working electrode 26 and the counter electrode 27 mostly extend longitudinally of the substrate 22, with their respective ends 26a, 27a extending widthwise of the substrate 22. With this construction, each of the working electrode 26 and the counter electrode 27 have a shape of L as a whole. The working electrode 26 and the counter electrode 27 have their respective ends 26b, 27b serving as terminals for connection with the first and the second terminals 10a, 10b of the concentration measuring apparatus 1 (See FIG. 1.) The working electrode 26 and the counter electrode 27 are coated with an insulating film, with their respective ends 26a, 26b, 27a, 27b exposed however.

The reagent pad 28 is solid for example, and bridges between the ends 26a, 27a of the working electrode 26 and the counter electrode 27. The reagent pad 28 includes a relatively small amount of an oxidation-reduction enzyme dispersed in a relatively large amount of mediator (an electron transfer material).

The electron transfer material is provided by a complex of iron or of ruthenium for example. A usable iron complex is potassium ferricyanide for example whereas usable ruthenium complexes include those having a $NH_3$ as a ligand.

The oxidation-reduction enzyme is selected in accordance with the kind of target component or the object of measurement. Examples of the target component are glucose, cholesterol and lactic acid, and for these targets, the oxidation-reduction enzyme is provided by glucose dehydrogenase, glucose oxidase, cholesterol dehydrogenase, cholesterol oxidase, lactate dehydrogenase, and lactate oxidase.

With the biosensor 2 constructed as the above, when a sample fluid is introduced via the sample liquid entrance 25a, the sample fluid moves through the passage 25 due to capillarity. During this, the sample fluid dissolves the reagent pad 28, thereby establishing a liquid phase reaction system in the passage 25, in which the oxidation-reduction enzyme helps remove electrons from the specific component of the sample fluid, whereby the specific component is oxidized. The released electrons are supplied to the electron transfer material, whereby the electron transfer material in the oxidized form is changed into the reduced form.

The first and the second terminals 10a, 10b in FIG. 1 are contacted by the ends 26b, 27b of the working electrode 26 and the counter electrode 27 respectively, when the biosensor 2 is attached to the concentration measuring apparatus 1.

The voltage applier 11 applies a voltage between the terminals 26b, 27b of the biosensor 2 via the first and the second terminals 10a, 10b. The voltage applier 11 is electrically connected with the first and the second terminals 10a, 10b. When the biosensor 2 is attached to the concentration measuring apparatus 1, the voltage applier 11 forms an electric circuit 17 together with the working electrode 26 and the counter electrode 27 of the biosensor 2 as well as with the reagent pad 28 (liquid phase reaction system). The voltage applier 11 includes a DC power source such as a non-rechargeable or rechargeable battery.

The electric current measurer 12 measures a value of an electric current when the voltage applier 11 applies the voltage between the terminals 26b, 27b of the biosensor 2. The electric current measurer 12 forms the electric circuit 17 together with the voltage applier 11 and the biosensor 2. Therefore, the electric current measurer 12 can measure an electric current passing through the electric circuit 17 even if the source voltage at the voltage applier 11 is turned to 0 volt.

The detector 13 detects if the reagent pad 28 has been supplied with the sample fluid, based on the electric current measurement made by the electric current measurer 12 after the biosensor 2 is attached to the concentration measuring apparatus 1.

The controller 14 controls the voltage applier 11, thereby selecting from the state in which the voltage is applied between the working electrode 26 and the counter electrode 27, and the sate in which the voltage is not.

The arithmetic processor 15 serves as a timer and calculator which calculates the concentration of the specific component in the sample fluid as well as correction values necessary for the calculation, in accordance with the electric current measurement made by the electric current measurer 12. The arithmetic processor 15 uses an amperometric technique for example, in calculating the concentration of the specific component.

Each of the detector 13, the controller 14 and the arithmetic processor 15 is provided by a CPU and a memory (such as a ROM or a RAM). However, all of the detector 13, the controller 14 and the arithmetic processor 15 may be provided by a single CPU and a plurality of memories connected thereto.

The display 16 displays results of the calculation performed by the arithmetic processor 15, as well as error messages, operation procedures, and so on, and is provided by a liquid crystal display for example.

Figure 5:
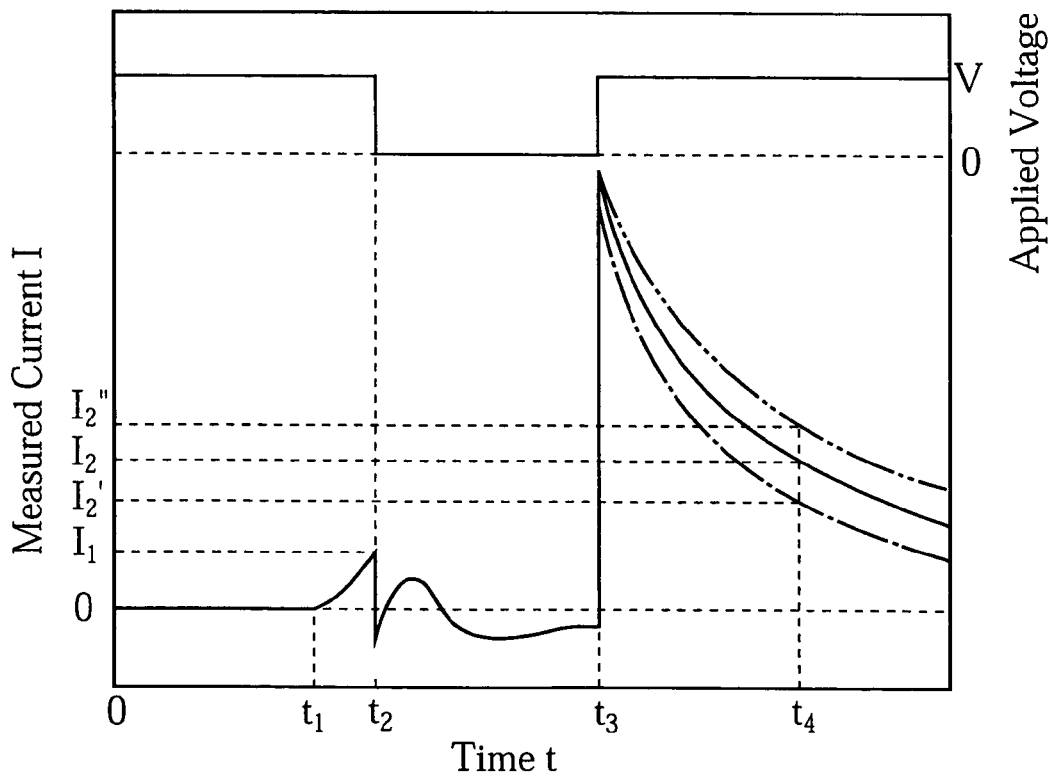
FIG. 5 is a graph showing an example of changes in a measured electric current along with changes in a voltage applied during a concentration measurement.

As described in the Background Art, when an amperometric technique is used in the concentration measurement with the biosensor 2, as shown in FIG. 5 by a single-dot chain line and a double-dot chain line, the response current obtained in actual measurement can be smaller (FIG. 5, $I_2'$) or larger (FIG. 5, $I_2''$) than the real value $I_2$. The inventors of the present invention have found that the deviation ($I_2'$-$I_2$, $I_2''$-$I_2$) has a relationship with an average or cumulative value of electric current measurements during the time period (FIG. 5, $t_2 \rightarrow t_3$) in which the voltage application to the reagent pad 28 (liquid phase reaction system) is stopped.

Figure 4:
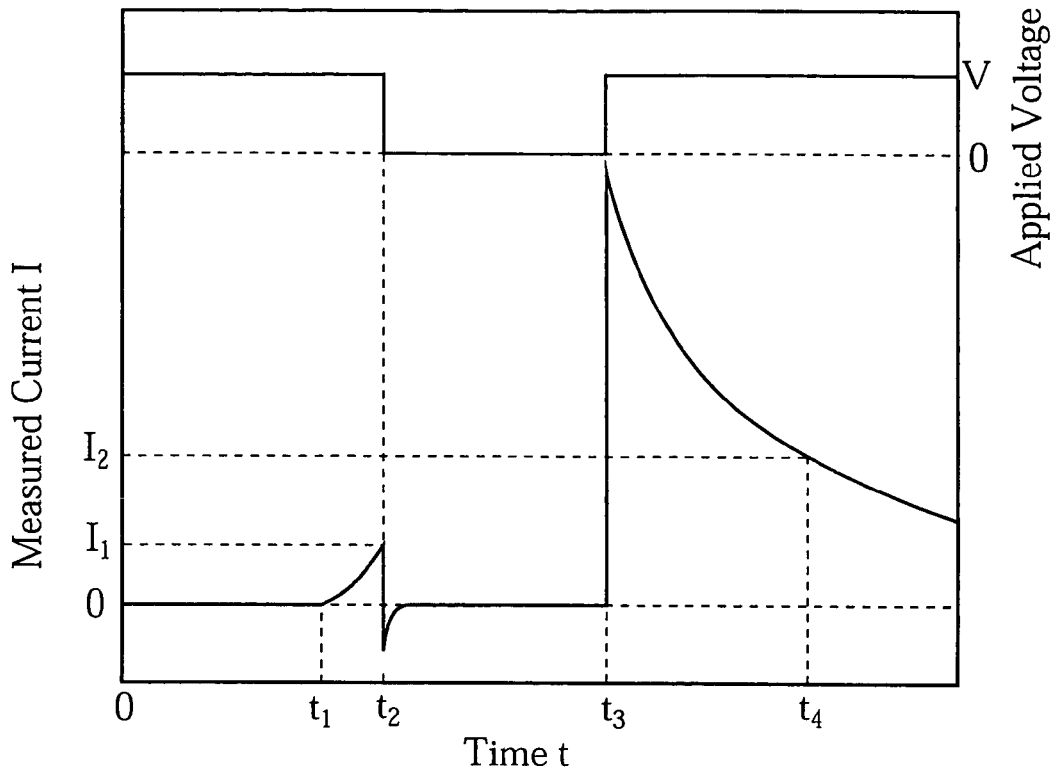
FIG. 4 is a graph showing an example of changes in a measured electric current along with changes in a voltage applied during a concentration measurement.

For example, as shown in FIG. 1 and FIG. 4, during the de-energized period (FIG. 4, $t_2 \rightarrow t_3$), since there is no voltage applied between the pair of electrodes 26, 27, the electric circuit 17 is ideally equal to an open circuit, and therefore no electric current flows through the electric circuit 17. Thus, upon stopping the voltage application between the pair of electrodes 26, 27 (FIG. 4, $t_2$), the electric current flowing through the electric circuit 17 changes the direction and then comes to zero instantaneously. However, if the electric circuit 17 is not perfectly equal to an open circuit, and if there is an electric potential difference in the electric circuit 17 during the de-energized period (FIG. 4, $t_2 \rightarrow t_3$), the electric potential difference will cause the electron transfer material in the reagent pad 28 (liquid phase reaction system) to be oxidized or reduced. If this happens, an electric current will flow in the electric circuit 17 as shown in FIG. 5. In this case, the state of flow in the electric current which has flown through the electric circuit 17 during the de-energized period (FIG. 4, $t_2 \rightarrow t_3$), is reflected as a measurement error. Therefore, it is possible to make correction, based on the state of flow in the electric current which has flown through the electric circuit 17 during the de-energized period (FIG. 4, $t_2$-$t_3$), e.g. an average or cumulative value of measured currents during the period, in order to obtain a more accurate value in the measurement.

Figure 6:
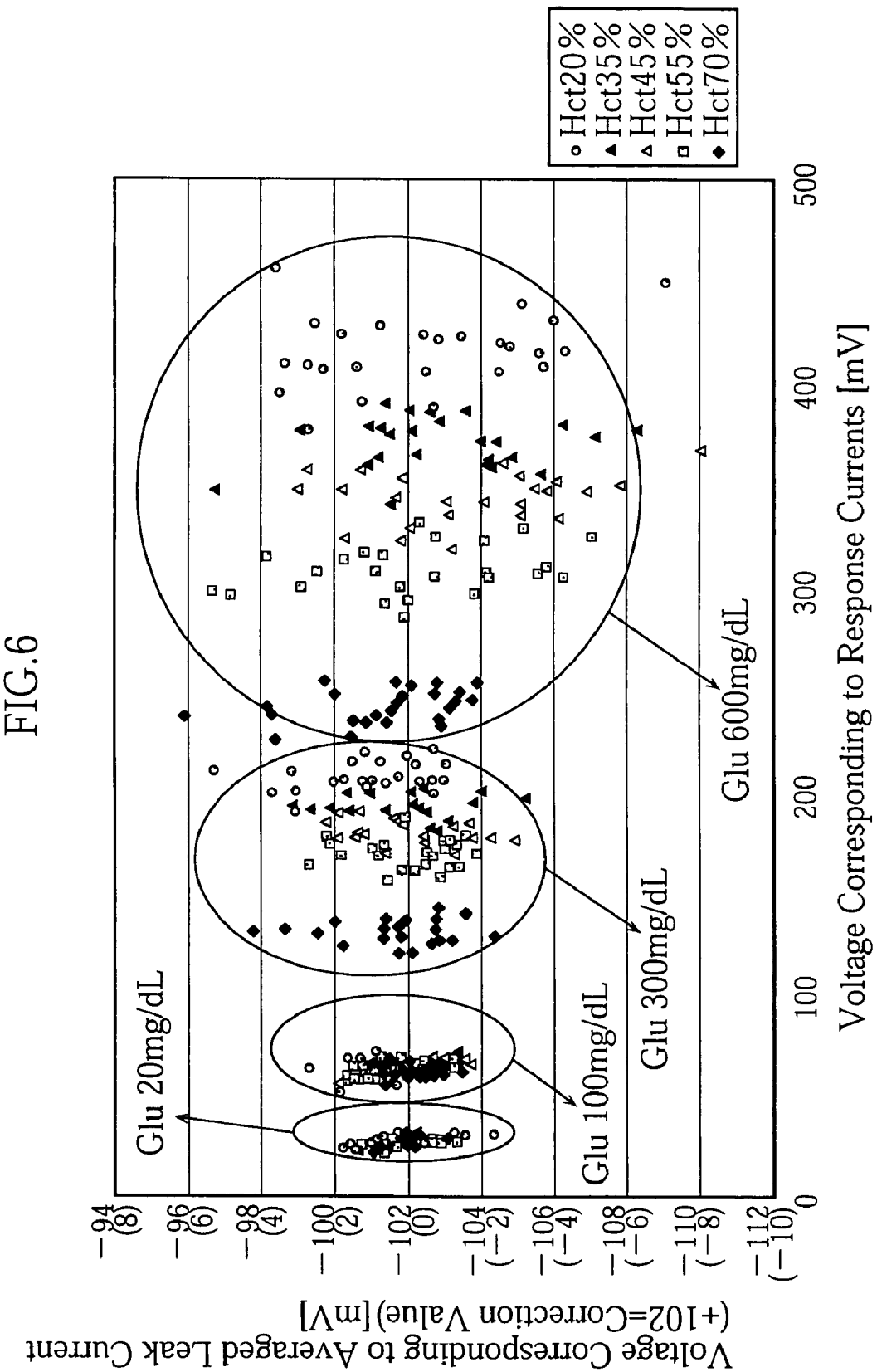
FIG. 6 is a graph showing a relationship between voltages corresponding to an average leak current and voltages corresponding to the response current, when a voltage is not applied.

The inventors of the present invention made measurements of the response current for a number of sample fluids of known glucose levels and hematocrit levels, using 25 biosensors. The response currents were measured in a pre-determined period of time since voltage application was resumed. The de-energized time period ($t_2 \rightarrow t_3$) was 25 seconds, and the measurement of the response current was made in five seconds (=$t_4$-$t_3$) after the voltage was resumed. The glucose level used was selected from 20 mg/dL, 100 mg/dL, 300 mg/dL or 600 mg/dL, whereas the hematocrit value was selected from Hct 20%, Hct 45%, Hct 55%, or Hct 70%. A total of 20 kinds of sample fluid were subjected to the measurement. Results are shown in FIG. 6. In this figure, the response current was converted to voltages and is shown on the horizontal axis, while the vertical axis gives voltages corresponding to an average of leak currents measured during the de-energized period. (Note that numbers in parentheses along the vertical axis show voltages (=corrected values) obtained by adding a value of 102 as a constant.)

As understood from FIG. 6, in all of the different groups, each consisting of measurements to the same glucose and the hematocrit levels by the 25 samples, there is a common tendency that the response current (or the corresponding voltage) increases along with decrease in the average current (or the corresponding voltage) during the de-energized period. Therefore, each sample group of the same glucose and hematocrit levels shows a negative gradient as a whole in FIG. 6. These results indicate that there is a correlation between the average leak current and the amount of error, and it is therefore possible to reduce the amount of error based the average value of the leak current. More specifically, if the average leak current is relatively large, the measured concentration tends to be lower, whereas the measured concentration tends to be higher if the average leak current is relatively small. Therefore, a positive correction (voltage) should be added when the average value of leak current is relatively large and a negative correction (voltage) should be added when the average value of leak current is relatively small, in order to make the gradient closer to vertical, which will then enable to obtain measurements less affected by the residual electric potentials during the de-energized period.

According to the present embodiment, as shown in parentheses in FIG. 6, a voltage correction value is obtained by adding a constant value of 102 to a given voltage converted from an average current. When calculating the glucose level in this case, the response current is converted to the response voltage, then the voltage correction value is added to the response voltage to get a corrected voltage, and the calculation of the glucose level is based on this corrected voltage. It should be noted here that the constant value 102 is a value obtained by the inventors of the present invention through trial-and-error attempts to make the negatively slanted groups of 25 samples generally vertical as a whole with respect to the horizontal axis.

In order to confirm effectiveness of the correction according to the present embodiment, actual corrections were made in all of the sample groups in FIG. 6 for each glucose level, and results are shown in FIG. 7. FIG. 7 gives an average of converted voltages corresponding to response currents, a standard deviation, and a reproducibility value (relative standard deviation) for the sample groups each consisting of 25 samples. The values are given for both before and after the correction.

As understood from FIG. 7, both standard deviation and reproducibility values are smaller after the correction than before, confirming that the correction is effective. Results shown in FIG. 7 also suggest that each sample group, consisting of 25 samples and having a negative gradient, will become generally vertical to the horizontal axis.

In the above, glucose was the specific component in the verification made on effectiveness of the correction. Such a correction, however, is applicable widely to cases in which an oxidation-reduction reaction is utilized for measurement of a concentration from a given current (voltage). In these cases, the correction value must be determined for each system of reaction, since different reaction system has a different cyclic voltammetry characteristic (CV characteristic) which determines how easily and quickly the reaction proceeds in the reduction/oxidation reaction. Further, it should be noted here that a cumulative value of the leak current is correlated with an average value of the leak current, and therefore a correction value can also be determined from a cumulative value of the leak current, from which essentially the same results will be obtained as in the case where the correction value is determined from an average value of the leak current.

An average or cumulative value of the leak current can be understood as a reflection of CV characteristic which determines how easily and quickly the reaction proceeds in the reduction/oxidation reaction. In other words, the size of the average or the accumulation of leak current is a reflection indicating how far away the response current is from the real value due to the leak current. Therefore, taking into account an average or cumulative value of the leak current in concentration calculation enables appropriate correction to be made on the measuring error caused by the leak current.

Figure 8:
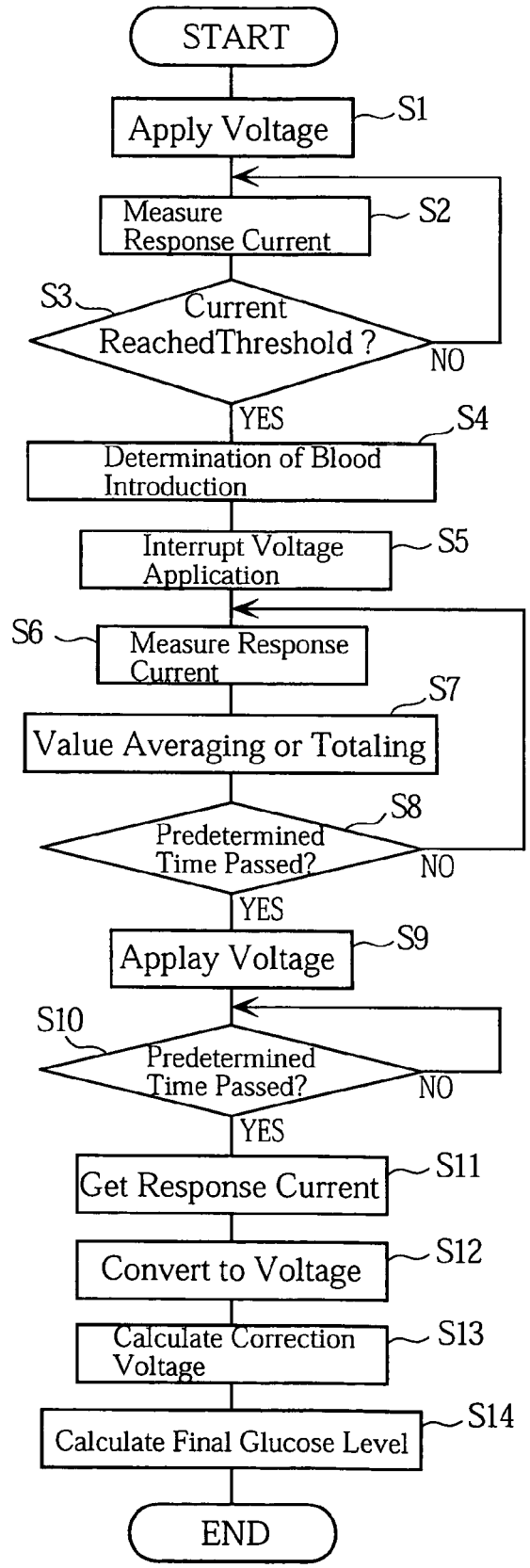
FIG. 8 is a flowchart for describing a concentration measuring process.

Next, description will be made for a method of measuring a concentration which incorporates the above-described verification results. The description will take an example of measuring a blood glucose level (blood glucose level), with reference to FIG. 1 through FIG. 5 as well as a flowchart in FIG. 8.

When measuring the blood glucose level, first, a biosensor 2 is attached to a concentration measuring apparatus 1, and the blood is introduced into the passage 25 via the sample liquid entrance 25a of the biosensor 2.

Meanwhile in the concentration measuring apparatus 1, the controller 14 controls the voltage applier 11 to apply a constant voltage between the pair of electrodes 26, 27 (S1) At this time, the electric current measurer 12 measures a value of response current (S2). The voltage applied in Step S1 is a constant voltage of 500 mV for example.

The detector 13 checks if the response current has reached a predetermined threshold value $I_1$ (See FIG. 4 and FIG. 5.) (S3). When the detector 13 does not determine that the response current has reached the threshold value $I_1$ (S3: NO), the detector 13 repeats the cycle of measuring a value of the current in S2 and checking the value in S3 until the detector 13 finds that the response current has reached the threshold value $I_1$ (S3: YES). In this cycle, the measurement of the response current in S2 is made every 0.05-0.2 seconds. However, if the detector 13 has finished a predetermined number of measuring cycles or continues to find no liquid conduction after a predetermined period of time, then the program may go to an error processing routine.

When the detector 13 sees that the measured current has reached the threshold value $I_1$, (S3: YES), this is a sign that the ends 26a, 27a of the working electrode 26 and the counter electrode 27 has been connected by a liquid conduction, i.e. the reagent pad 28 has been supplied with the blood. Thus, the detector 13 determines that the blood has been introduced into the reagent pad 28 (S4).

Next, the controller 14 stops the application of voltage from the voltage applier 11 to the working electrode 26 and the counter electrode 27 (S5). Such a stoppage of the voltage supply is made by setting a power source voltage to 0 volt at the power source included in the voltage applier 11.

Meanwhile in the passage 25, the blood dissolves the reagent pad 28, to constitute a liquid phase reaction system. In the liquid phase reaction system, blood glucose is oxidized while the electron transfer material is reduced for example. During the time when the voltage application to the working electrode 26 and the counter electrode 27 is stopped, the reduced electron transfer material accumulates without being oxidized.

The electric current measurer 4 continues to measure the response currents under the state where the voltage application is not made between the working electrode 26 and the counter electrode 27 (de-energized state: FIG. 4 and FIG. 5, $t_2 \rightarrow t_3$) (S6). Every time the response current is measured in S6, the arithmetic processor 15 calculates an average value or an cumulative value of the response currents (S7), while counting the time since the voltage application was stopped and checking if a predetermined amount of time, e.g. 25 seconds (=$t_3$-$t_2$ (See FIG. 4 and FIG. 5.)), has passed (S8).

When the arithmetic processor 15 does not determine that the predetermined amount of time has been passed since the voltage application was stopped, (S8: NO), the arithmetic processor 15 repeats the cycle of measuring a current in S6 and the calculation of an average or cumulative value of the response currents in S7 until the arithmetic processor 15 determines that the predetermined amount of time has been passed (S8: YES). The measurement of the response current in S6 is made every 0.05-0.2 seconds.

When the arithmetic processor 15 determines that the predetermined amount of time has passed since the voltage application was stopped, (S8: YES), a constant voltage of 500 mV for example is applied between the working electrode 26 and the counter electrode 27 (S9) by the voltage applier 11 under the control by the controller 14. This allows the reduced electron transfer material to release the electrons to the end 26a of the working electrode 26, thereby oxidized.

The arithmetic processor 15 counts the time since the voltage application, and determines if a predetermined amount of time, e.g. 5 seconds (=$t_4$-$t_3$ (See FIG. 4 and FIG. 5)) has passed (S10). When the arithmetic processor 15 does not determine that the predetermined amount of time has passed (S10: NO), the arithmetic processor 15 repeats the cycle of checking in S10 until the arithmetic processor 15 determines that the predetermined amount of time has been passed (S10: YES).

When the arithmetic processor 15 determines that the predetermined amount of time has passed (S10: YES), the arithmetic processor 15 obtains a value of electric current measured by the electric current measurer 12 at this point (S11), and converts the value into a response voltage (S12).

Next, the arithmetic processor 15 calculates a voltage correction value (S13) based on the average or cumulative value of the measurements during the de-energized period (FIG. 4 and FIG. 5, $t_2 \rightarrow t_3$). The calculation of the correction value is made as described earlier, by converting the averaged or cumulative value of the current measurements (leak current) during the de-energized period into a voltage and adding the constant 102 to the obtained voltage.

Finally, from the corrected voltage obtained by adding the voltage correction value to the response voltage, the arithmetic processor 15 calculates the final target value of glucose level (S14). The calculation of the glucose level is based on a predetermined calibration curve or lookup table which correlates the voltage with glucose level. The obtained result is displayed on the display 16 for example.

According to the concentration calculation method described above, the error caused by electric current passing through the electric circuit 17 while the circuit is de-energized is corrected based upon an average or cumulative value of the leak current which is a correlated value with the amount of the error. Therefore, the above concentration calculation method enables to decrease accuracy deterioration caused by leak current when the voltage is not applied.

Alternatively, the arithmetic processor may use one of the following methods in the concentration calculation. Specifically, in a first method, a current correction value is calculated by adding a constant to an average or accumulated value of leak current measurements during the de-energized period, and then the current correction value is added to the response current to obtain a corrected current, and a glucose level is calculated from this corrected current. In a second method, a preliminary value of glucose level is calculated based on the response current (or a response voltage converted from the response current), then a concentration correction value is calculated from an average or cumulative value of the leak current measurements (or a voltage obtained converted from these), and finally the concentration correction value is added to the preliminary concentration to obtain the final glucose level.

The present embodiment uses an amperometric technique in the measurement of glucose level, and the description was made accordingly. The present invention is also applicable to measurement of a specific component using a coulometric technique (cumulative value of response current).

The invention claimed is:

1. A method for measuring a concentration of a specific component, comprising:
a first step of supplying a sample fluid to a reaction field holding a reagent;
a second step of obtaining a single or a plurality of leak currents for correction, through a measurement of electric current made once or a plurality of times without applying a voltage to the reaction field from a voltage applier and without opening a mechanical switch;
a third step of obtaining a single or a plurality of electric currents for calculation, through a measurement of electric current made once or a plurality of times while applying a voltage to the reaction field; and
a fourth step of calculating a concentration of a specific component in the sample fluid, based on the single or the plurality of values for correction and the single or the plurality of values for calculation.

2. The method according to claim 1, wherein the fourth step reflects an average or cumulative value of the leak currents for correction on a calculated result of the concentration of the specific component.

3. The method according to claim 2, wherein the fourth step includes: calculation of a correction constant based on the leak currents for correction; conversion of the single leak current for calculation into a voltage for calculation, calculation of a corrected voltage by adding the correction constant to the voltage for calculation; and calculation of a final concentration of the specific component from the corrected voltage.

4. The method according to claim 3, wherein the calculation of the correction constant is made by adding a constant to one of the values selected from: a first voltage conversion value for correction given as an average of voltage conversion values converted from the measurements for correction; a second voltage conversion value for correction given as a cumulative value of the voltage conversion values converted from the measurements for correction; and a third voltage conversion value for correction given as a voltage conversion value converted from an average or cumulative value of the leak currents for correction.

5. The method according to claim 2, wherein the fourth step includes: calculation of a correction constant based on an average or cumulative value of the leak currents for correction; calculation of a corrected current by adding the correction constant to the electric current for calculation; and calculation of a final concentration of the specific component based on the corrected current.

6. The method according to claim 2, wherein the fourth step includes: calculation of a preliminary concentration of the specific component from the single or the plurality of electric currents for calculation; calculation of a correction constant based on an average or cumulative value of the leak currents for correction; and calculation of a final concentration of the specific component by adding the correction constant to the preliminary concentration.

7. The method according to claim 1, wherein the reagent contains an oxidation-reduction enzyme and an electron transfer material.

8. The method according to claim 1, wherein the sample fluid is provided by blood.

9. The method according to claim 1, wherein the specific component is glucose.

10. A concentration measuring apparatus for measurement of a concentration of a specific component in a sample fluid by using a measuring tool for holding the sample fluid and providing a reaction field, the measuring tool including a first and a second electrodes for application of a voltage to the reaction field,
the apparatus comprising:
a voltage applier for application of a voltage to the reaction field;
a controller for selection from an energized state in which the voltage is applied to the reaction field and a de-energized state in which a voltage is not applied to the reaction field from the voltage applier without opening a mechanical switch;
an electric current measurer for measurement of an electric current for calculation, by using the first and the second electrodes; and
an arithmetic processor for calculation of a concentration of the specific component based on the electric current for calculation,
the controller selecting the de-energized state for a specific duration of time after a supply of the sample fluid to the reaction field, and selecting the energizing state for at least a predetermined period of time after passage of the specific duration of time,
the electric current measurer obtaining a single or a plurality of leak currents for correction through a measurement of electric current made once or a plurality of times during the specific duration of time,
the arithmetic processor calculating the concentration of the specific component while taking into account the single or the plurality of leak currents for correction.

11. The apparatus according to claim 10, wherein the arithmetic processor reflects an average or cumulative value of the measurements on a calculated result of the concentration of the specific component.

* * * * *